United States Patent
Suzuki et al.

(10) Patent No.: US 6,875,401 B1
(45) Date of Patent: Apr. 5, 2005

(54) AUTOMATIC ANALYZER

(75) Inventors: Youichirou Suzuki, Hitachinaka (JP); Shigenori Watari, Hitachinaka (JP); Hajime Kato, Ibaraki (JP); Hiroyasu Uchida, Hitachinaka (JP); Katsuhiro Kanbara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/936,940
(22) PCT Filed: Feb. 23, 2000
(86) PCT No.: PCT/JP00/01019
§ 371 (c)(1), (2), (4) Date: Nov. 14, 2001
(87) PCT Pub. No.: WO01/63300
PCT Pub. Date: Aug. 30, 2001

(51) Int. Cl.$^7$ ................................. B01F 11/02
(52) U.S. Cl. ..................... 422/63; 422/64; 422/67; 422/99; 366/108; 366/127; 436/174
(58) Field of Search .................. 422/63, 64, 67, 422/99; 366/108, 127; 436/174

(56) References Cited

U.S. PATENT DOCUMENTS 4,602,184 A * 7/1986 Meitzler ................ 310/322
5,276,376 A * 1/1994 Puskas ................... 310/317
5,736,100 A * 4/1998 Miyake et al. ............ 422/64
2001/0019702 A1 * 9/2001 Watari et al. ............. 422/67
2003/0166260 A1 * 9/2003 Katou et al. ........... 435/287.1

FOREIGN PATENT DOCUMENTS

| JP | 2-67963 | 3/1990 |
| JP | 8-146007 | 6/1996 |
| JP | 11-230970 | 8/1999 |

* cited by examiner

Primary Examiner—Jan M. Ludlow
(74) Attorney, Agent, or Firm—Mattingly, Stanger, Malur & Brundidge, P.C.

(57) ABSTRACT

A sample, a reagent, etc. in a reaction container 132 is agitated with an ultrasonic wave generated from a piezoelectric transducer (141, 142). A power supply unit (144) applies, to the piezoelectric transducer, a voltage having been subjected to frequency modulation at frequencies over an optional frequency range. An analyzing section (130) measures a reaction product produced as an analysis target from the reagent, etc. and the sample under agitation, and then analyzes components of the sample. With such a construction, adjustment work needed in an agitating section can be simplified, and satisfactory analyzed results can be obtained regardless of differences in frequency characteristics of ultrasonic wave generators used for ultrasonic agitation.

9 Claims, 9 Drawing Sheets

AUTOMATIC ANALYZER

TECHNICAL FIELD

The present invention relates to an automatic analyzing apparatus for analyzing components of a sample using a reagent, etc., and more particularly to an automatic analyzing apparatus provided with agitating means suitable for agitating a sample, a reagent, etc.

BACKGROUND ART

In conventional automatic analyzing apparatuses, an agitating method using ultrasonic waves is known as one of methods for agitating a sample, a reagent, etc. Several examples of the agitating method using ultrasonic waves are as follows. 1) A method of making cohesion of substances under agitation less likely to occur by utilizing a phenomenon that an ultrasonic wave acts upon a portion in which a difference in acoustic impedance is large, as disclosed in, e.g., JP A, 2-67963. 2) A method of vibrating a container itself and providing an agitation capability, as disclosed in, e.g., JP A, 11-230970. 3) A method of giving rise to convection due to an acoustic flow of substances themselves under agitation caused upon irradiation of an ultrasonic wave, as disclosed in, e.g., JP A, 8-146007. Those agitating methods using ultrasonic waves have advantages that since a sample, a reagent, etc. can be agitated in a contactless manner, there is no fear of contaminating other samples, reagents, etc., and that since any agitating rod is not required, the size of a reaction container can be reduced and the amounts of the sample and reagent consumed can be reduced.

DISCLOSURE OF THE INVENTION

In any of the above-mentioned conventional methods, however, the agitation capability depends on characteristics of ultrasonic wave generators used. Even when a voltage having the same amplitude and frequency is applied to drive each of ultrasonic wave generators, the intensities of sound pressures of ultrasonic waves generated from the ultrasonic wave generators change due to differences in individual frequency characteristics and variations in resonance frequency, thus causing differences in agitation states and analyzed results. In order to obtain stable analyzed results, therefore, it is required to adjust ultrasonic outputs of the individual ultrasonic wave generators. Thus, a first problem with the conventional methods is that the adjustment requires a skill and hence adjustment work takes a time.

Also, after an ultrasonic wave generator has been equipped in an analyzing apparatus, the resonance frequency of the ultrasonic wave generator changes due to flaws, depolarization, deteriorations, etc. occurred in the ultrasonic wave generator during repeated operations. Thus, a second problem is that a readjustment is required to compensate for such changes of the frequency characteristic over time and maintainability is poor.

A first object of the present invention is to provide an automatic analyzing apparatus, which can simplify adjustment work needed in an agitating section, and can ensure satisfactory analyzed results regardless of differences in frequency characteristics of ultrasonic wave generators used for ultrasonic agitation.

A second object of the present invention is to provide an automatic analyzing apparatus, which can eliminate the necessity of a readjustment to compensate for, e.g., changes in characteristics of an ultrasonic wave generator over time, and has improved maintainability.

(1) To achieve the first object, the present invention provides an automatic analyzing apparatus comprising an agitating section for agitating a sample, a reagent, etc. with an ultrasonic wave generated from an ultrasonic wave generator, and an analyzing section for measuring a reaction product produced as an analysis target from the reagent, etc. and the sample under agitation, and analyzing components of the sample, wherein the agitating section includes a power supply unit for applying, to the ultrasonic wave generator, a voltage having been subjected to frequency modulation at frequencies over an optional frequency range. With that construction, adjustment work needed in the agitating section can be simplified, and satisfactory analyzed results can be obtained regardless of differences in frequency characteristics of the ultrasonic wave generator used for ultrasonic agitation.

(2) In above (1), preferably, the ultrasonic wave generator in the agitating section comprises a first ultrasonic wave generator disposed below a reaction container for containing the sample, the reagent, etc., and a second ultrasonic wave generator disposed laterally of the reaction container, and the power supply unit applies, to at least the second ultrasonic wave generator, a voltage having been subjected to frequency modulation.

(3) In above (1), preferably, the automatic analyzing apparatus further comprises a sensor for measuring the intensity of the ultrasonic wave irradiated to the sample, the reagent, etc. from the ultrasonic wave generator, and a control unit for controlling the power supply unit so that the intensity of the ultrasonic wave detected by the sensor is held at a predetermined intensity. With that construction, the necessity of a readjustment to compensate for, e.g., changes in characteristics of the ultrasonic wave generator over time is eliminated, and maintainability can be improved.

(4) In above (3), preferably, the control unit varies a frequency range and a central frequency of a voltage applied from the power supply unit to the ultrasonic wave generator.

(5) In above (3), preferably, the control unit varies an amplitude of a voltage applied from the power supply unit to the ultrasonic wave generator.

(6) In above (3), preferably, the control unit issues an alarm indicating the occurrence of any abnormality in the agitating section if the detected intensity of the ultrasonic wave cannot be held at the predetermined intensity in spite of control of the power supply unit.

BEST MODE FOR CARRYING OUT THE INVENTION

The construction of an automatic analyzing apparatus according to one embodiment of the present invention will be described below with FIGS. 1 to 12.

Figure 1:
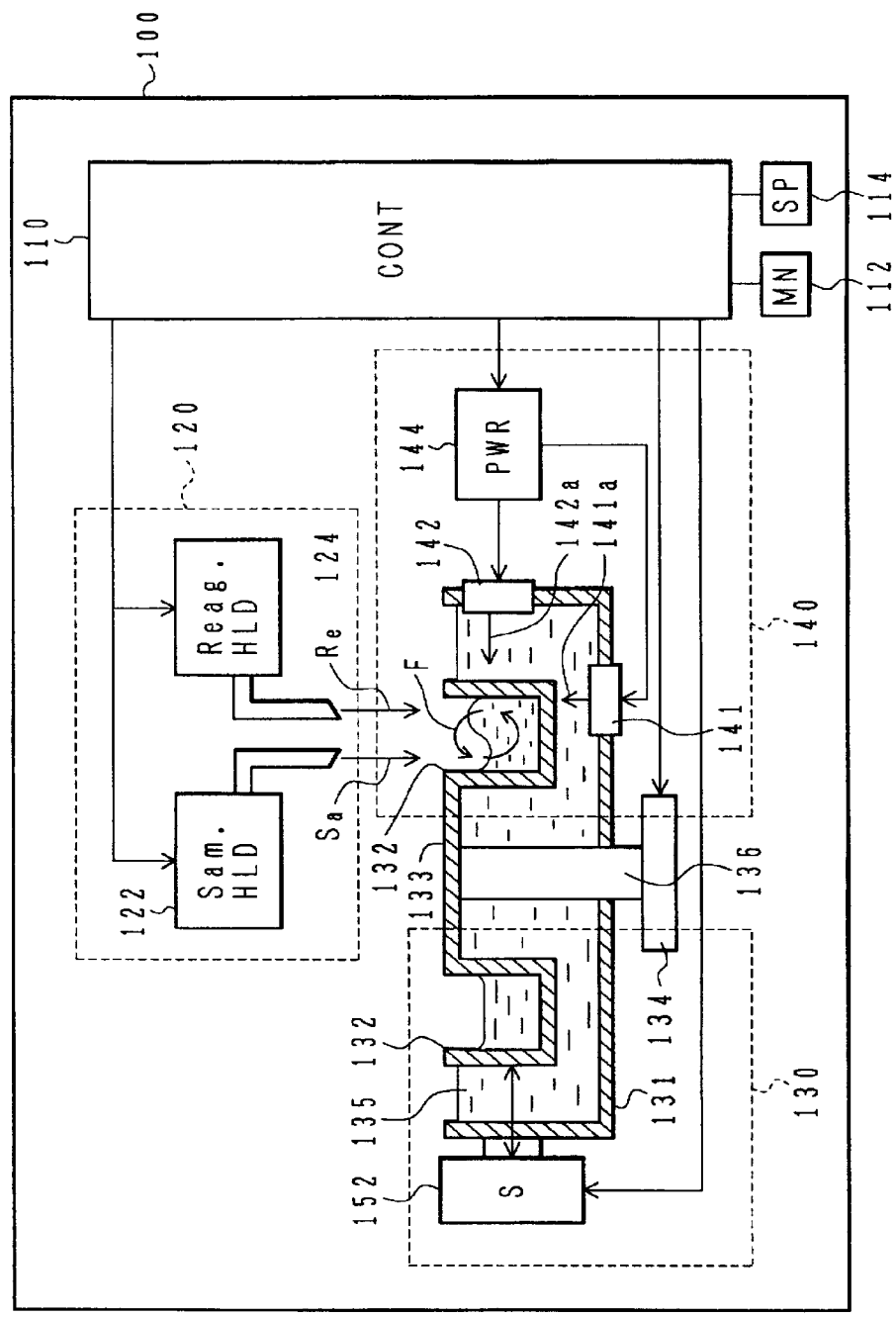
FIG. 1 is a block diagram showing the overall construction of an automatic analyzing apparatus according to one embodiment of the present invention.

A description is first made of the overall construction of the automatic analyzing apparatus of this embodiment with reference to FIG. 1.

FIG. 1 is a block diagram showing the overall construction of the automatic analyzing apparatus according to one embodiment of the present invention.

An automatic analyzing apparatus 100 comprises a control unit 110, a holding section 120, a reaction section 130, an agitating section 140, and an analyzing section 150. The control unit 110 comprises an electronic circuit and a storage device for executing detailed operation control of the respective sections, and controls the operation of the apparatus in a supervising manner. A monitor 112 and a speaker 114 are connected to the control unit 110. The holding section 120 comprises a sample holding unit 122 containing a sample Sa and a regent holding unit 124 containing a reagent Re.

The reaction section 130 comprises a reaction tank 131, a plurality of reaction containers 132, a reaction disk 133, and a reaction disk motor 134. A temperature maintaining medium 135 typically represented by water is filled in the reaction tank 131. The plurality of reaction containers 132 arranged on the reaction disk 133 are held in the temperature maintaining medium 135 and are kept at a predetermined temperature. The reaction disk 133 is coupled to the reaction disk motor 134 through a reaction disk shaft 136 and driven by it. The control unit 110 controls the reaction disk motor 134 for rotating or moving the reaction disk 133 and the reaction containers 132 together so that the reaction containers 132 reciprocate between the agitating section 140 and the analyzing section 150.

The agitating section 140 comprises piezoelectric transducers 141, 142 and a power supply unit 144. The agitating section 140 agitates the sample ejected from the sample holding unit 122 into each reaction container 132 and the reagent Re ejected from the regent holding unit 124 into each reaction container 132 with the aid of swirl flows F that are caused based on effects of acoustic radiant pressures due to ultrasonic waves 141a, 142a generated from the piezoelectric transducers 141, 142. The piezoelectric transducer 141 is disposed below the reaction container 132 to irradiate the ultrasonic wave 141a from below so that the liquid surface of a mixture of the sample Sa and the reagent Re rises. Also, the piezoelectric transducer 142 is disposed laterally of the reaction container 132 to irradiate the ultrasonic wave 142a toward the liquid in an area where the liquid surface rises with the ultrasonic wave from the piezoelectric transducer 141. The swirl flows F are thereby produced due to the acoustic radiant pressures for agitation of the mixture. The detailed construction of the power supply unit 144 in the agitating section 140 will be described later with reference to FIG. 2.

The analyzing section analyzes the composition of a product, which has been resulted from mixing and reaction of the sample Sa and the reagent Re in each of the reaction container 132 positioned in the analyzing section, by using a spectrometer 152.

The construction and operation of the agitating section of the automatic analyzing apparatus of this embodiment will be described below with reference to FIGS. 2 to 12.

Figure 2:
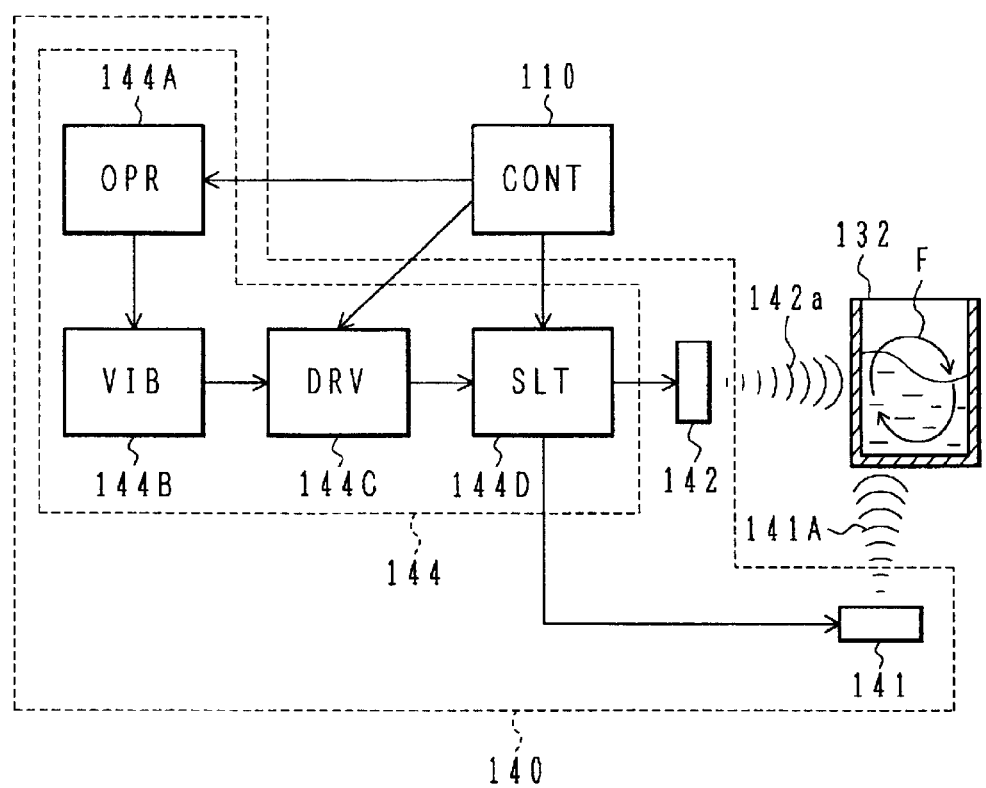
FIG. 2 is a block diagram showing the detailed construction of an agitating section of the automatic analyzing apparatus according to one embodiment of the present invention.

A description is first made of the detailed construction of the agitating section of the automatic analyzing apparatus of this embodiment with reference to FIG. 2.

FIG. 2 is a block diagram showing the detailed construction of the agitating section of the automatic analyzing apparatus according to one embodiment of the present invention. The same characters in FIG. 2 as those in FIG. 1 denote the same components.

The piezoelectric transducer 141 is disposed below the reaction container 132 to irradiate the ultrasonic wave 141a from below so that the liquid surface of the mixture of the sample 7 and the reagent Re rises. Also, the piezoelectric transducer 142 is disposed laterally of the reaction container 132 to irradiate the ultrasonic wave 142a toward the liquid in an area where the liquid surface rises with the ultrasonic wave from the piezoelectric transducer 141. The swirl flows F are thereby produced due to the acoustic radiant pressures for agitation of the mixture.

The power supply unit 144 comprises a vibration signal operating means 144A, a vibration applying circuit 144B, a drive circuit 144C, and a piezoelectric transducer selecting means 144D. The drive circuit 144C supplies electrical power for generating ultrasonic waves to the piezoelectric transducers 141, 142, whereupon the piezoelectric transducers 141, 142 generate the ultrasonic waves 141a, 142a. The piezoelectric transducer selecting means 144D is controlled by the control unit 110 so as to select one of the plurality of piezoelectric transducers 141, 142 for driving it, or to drive the plurality of piezoelectric transducers 141, 142 at the same time. Also, each of the piezoelectric transducers 141, 142 may be constituted by plural pieces of piezoelectric transducers. In such a case, the piezoelectric transducer selecting means 144D may be controlled by the control unit 110 so as to select one or more of the plural pieces constituting the piezoelectric transducer 141, or to select one or more of the plural pieces constituting the piezoelectric transducer 142. The vibration applying circuit 144B supplies drive signals to the drive circuit 144C for driving the piezoelectric transducers 141, 142. The vibration signal operating means 144A manages and changes the frequency and voltage amplitude of a vibration signal. Thus, the agitating section 140 is controlled by the control unit 110 for driving the piezoelectric transducers 141, 142 while varying the drive frequency of the piezoelectric transducer, the timing of generation of the ultrasonic wave, the intensity of the generated ultrasonic wave, etc., or while selecting the piezoelectric transducer to be driven. Details of the control of the agitating section 140 by the control unit 110 will be described later with reference to FIG. 3 and the subsequent figures.

The relationship between the frequency of a voltage applied to the piezoelectric transducer and the intensity of the generated ultrasonic wave will be described with reference to FIGS. 3 and 4.

Figure 3:
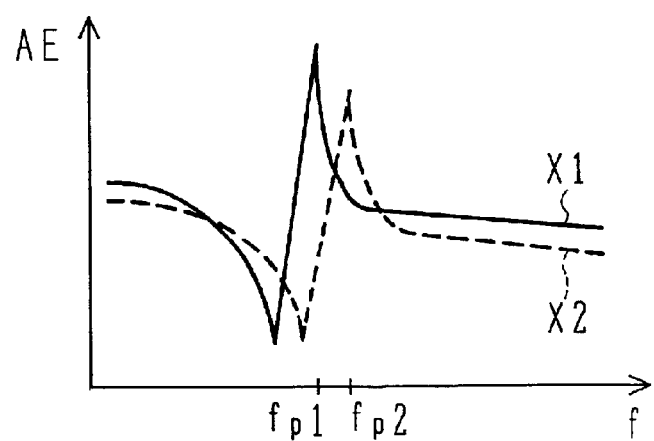
FIG. 3 is a chart for explaining the relationship between the frequency of a voltage applied to a piezoelectric transducer and the intensity of a generated ultrasonic wave, the piezoelectric transducer being used in the agitating section of the automatic analyzing apparatus according to one embodiment of the present invention.
Figure 4:
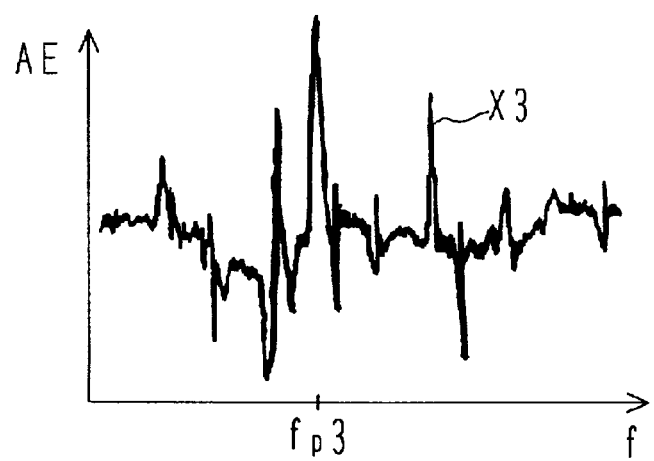
FIG. 4 is a chart for explaining the relationship between the frequency of a voltage applied to a piezoelectric transducer and the intensity of a generated ultrasonic wave, the piezoelectric transducer being used in the agitating section of the automatic analyzing apparatus according to one embodiment of the present invention.

FIGS. 3 and 4 are each a chart for explaining the relationship between the frequency of a voltage applied to the piezoelectric transducer and the intensity of the generated ultrasonic wave, the piezoelectric transducer being used in the agitating section of the automatic analyzing apparatus according to one embodiment of the present invention.

As shown in FIG. 3, the intensity of an ultrasonic wave generated from each piezoelectric transducer has a frequency characteristic containing a resonance frequency fp, i.e., a certain frequency at which the intensity of ultrasonic wave takes a maximum value. The resonance frequency fp differs slightly between individual piezoelectric transducers even if they are manufactured using the same material and process. For example, a characteristic X1 represents a frequency characteristic of one piezoelectric transducer and has a resonance frequency fp1. A characteristic X2 represents a frequency characteristic of another piezoelectric transducer that is manufactured using the same material and process, and has a resonance frequency fp2. Thus, the resonance frequency of the piezoelectric transducer 141 and the resonance frequency of the piezoelectric transducer 142, shown in FIG. 1, are not exactly in match with each other. Also, the resonance frequency of a piezoelectric transducer used in an agitating section of one automatic analyzing apparatus and the resonance frequency of a piezoelectric transducer used in an agitating section of another automatic analyzing apparatus are not exactly in match with each other. In order to obtain an identical agitation capability, therefore, it is required to decide the vibration signal for each piezoelectric transducer, and to adjust the voltage amplitude and frequency of the vibration signal.

Furthermore, as shown in FIG. 4, the intensity of an ultrasonic wave generated from some of used piezoelectric transducers may have a frequency characteristic containing several sharp peaks or being in disorder. For example, a characteristic X3 shown in FIG. 4 represents a frequency characteristic of one piezoelectric transducer and has a difficulty in specifying a resonance frequency fp3. Also, if the frequency of the vibration signal shifts upon effects of temperature changes and so on, the intensity of the generated ultrasonic wave drops abruptly and the expected agitation capability cannot be obtained in some cases.

The first operation of frequency modulation performed by the vibration signal operating means in the agitating section of the automatic analyzing apparatus of this embodiment will be described below with reference to FIGS. 5 to 7.

Figure 5:
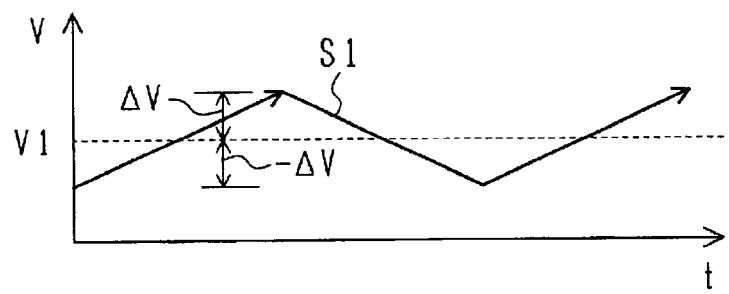
FIG. 5 is a waveform chart showing an output signal of a vibration signal operating means 144A in the agitating section of the automatic analyzing apparatus according to one embodiment of the present invention.
Figure 6:
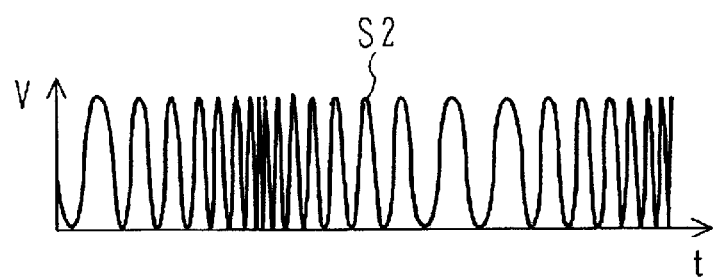
FIG. 6 is a waveform chart showing an output signal of a vibration applying circuit 144B in the agitating section of the automatic analyzing apparatus according to one embodiment of the present invention.
Figure 7:
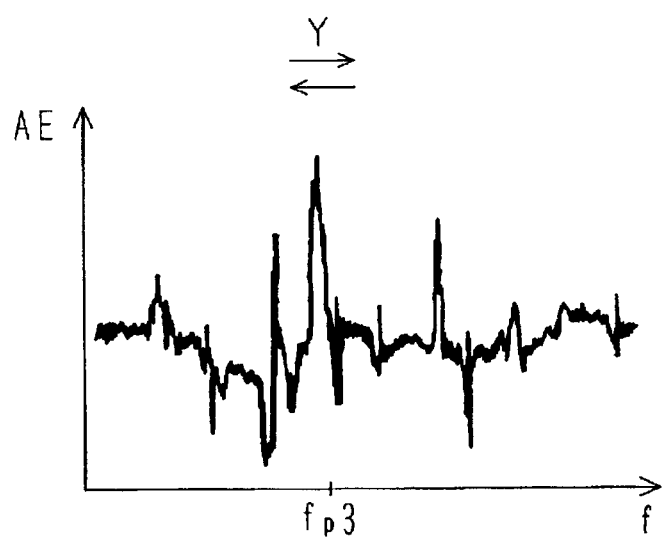
FIG. 7 is a chart for explaining the vibration applying operation performed in the agitating section of the automatic analyzing apparatus according to one embodiment of the present invention.

FIG. 5 is a waveform chart showing an output signal of the vibration signal operating means 144A in the agitating section of the automatic analyzing apparatus according to one embodiment of the present invention, FIG. 6 is a waveform chart showing an output signal of the vibration applying circuit 144B in the agitating section of the automatic analyzing apparatus according to one embodiment of the present invention, and FIG. 7 is a chart for explaining the vibration applying operation performed in the agitating section of the automatic analyzing apparatus according to one embodiment of the present invention.

In this embodiment, the power supply unit 144 changes the frequency of the vibration signal supplied to the piezoelectric transducers 141, 142. The vibration applying circuit 144B is constituted as a voltage controlled oscillation circuit. The oscillation frequency outputted from the voltage controlled oscillation circuit is held at a fixed frequency when a DC constant voltage is applied to it. Also, the oscillation frequency outputted from the voltage controlled oscillation circuit can be varied by applying a varying voltage to it.

In FIGS. 5 and 6, the horizontal axis represents a time t and the vertical axis represents a voltage V. As shown in FIG. 5, the vibration signal operating means 144A outputs a vibration operative signal S1 in the form of a triangular wave to the vibration applying circuit 144B. The voltage of the triangular wave varies from $-\Delta v$ to $+\Delta v$ about a center voltage V1.

By applying such a triangular wave, as shown in FIG. 6, a vibration signal S2 outputted from the vibration applying circuit 144B has the oscillation frequency that becomes higher as the voltage of the vibration operative signal rises, and becomes lower as it lowers. In the case of employing a triangular wave, since a change rate of the voltage is constant during the rising and lowering of the voltage, a change rate of the frequency is the same at any frequency. In other words, a time during which oscillation is applied is the same at any frequency within a region in which the oscillation frequency of the vibration signal varies.

Also, by providing an offset V1 to the vibration operative signal as shown in FIG. 5, the oscillation frequency of the vibration signal shown in FIG. 6 can be outputted within a frequency range of $\pm \Delta f$ about the center at the frequency fp3 corresponding to the offset voltage V1. Thus, as shown in FIG. 7, a region Y (fp3$\pm \Delta f$) in which the oscillation frequency varies is given by a frequency range of $\pm \Delta f$ with the resonance frequency fp3 of the piezoelectric transducer being at the center. In an illustrated example, the central frequency of the oscillation frequency varying region (fp3$\pm \Delta f$) is assumed to be in match with the resonance frequency fp3 of the piezoelectric transducer. As described above with reference to FIG. 3, however, the resonance frequency of the piezoelectric transducer differs slightly between individual piezoelectric transducers. Even with such a shift of the resonance frequency of the piezoelectric transducer to the higher or lower side from fp3, since the oscillation frequency is varied in this embodiment, the piezoelectric transducer can be vibrated at the resonance frequency to generate an ultrasonic wave without needing, e.g., a special adjustment of the oscillation frequency so long as the resonance frequency of the piezoelectric transducer is within the oscillation frequency varying region Y. Assuming, for example, that the resonance frequency fp3 of the piezoelectric transducer is 1.6 MHz and an error due to, e.g., variations of the resonance frequency fp3 caused during the manufacturing process is +3% (=48 kHz), the oscillation frequency varying region Y is set to 1.6 MHz±0.05 MHz. By so setting the oscillation frequency varying region Y, even when there occurs an error in the resonance frequency fp3 of the piezoelectric transducer due to, e.g., variations thereof caused during the manufacturing process, the resonance frequency of the piezoelectric transducer is always kept within the oscillation frequency varying region Y. Consequently, the piezoelectric transducer can be vibrated at the resonance frequency to generate an ultrasonic wave without needing, e.g., an adjustment of the oscillation frequency.

Additionally, using a triangular wave is advantageous in that, though depending on the shape of the reaction container and the viscosity of a liquid under analysis, the oscillation frequency of the triangular wave serves to produce pulsating fluctuations of the swirl flows at that frequency and to improve the agitation capability.

The second operation of frequency modulation performed by the vibration signal operating means in the agitating section of the automatic analyzing apparatus of this embodiment will be described below with reference to FIGS. 8 and 9.

Figure 8:
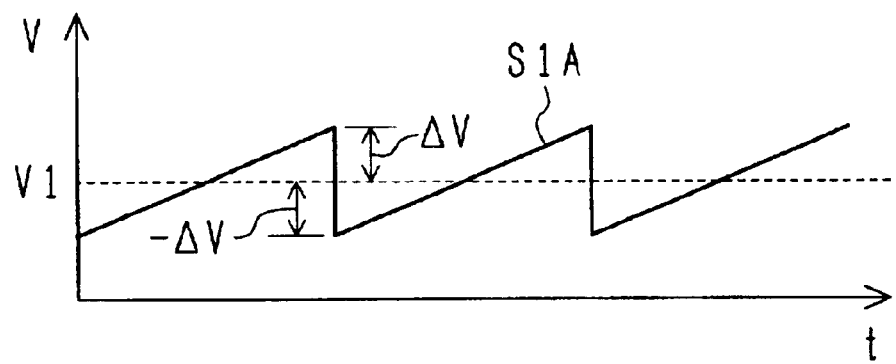
FIG. 8 is a waveform chart showing an output signal of the vibration signal operating means 144A in the agitating section of the automatic analyzing apparatus according to one embodiment of the present invention.
Figure 9:
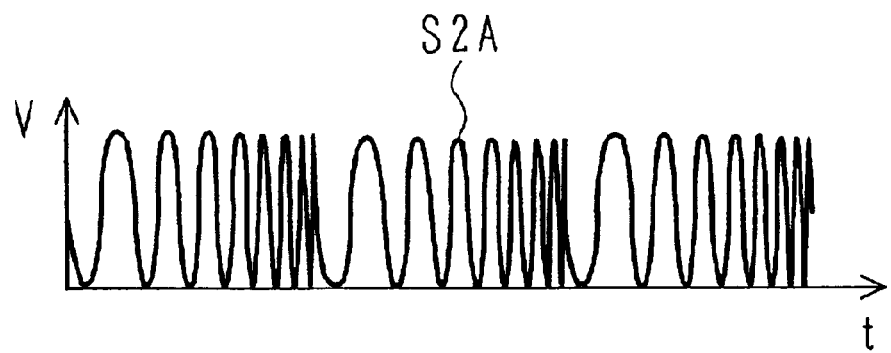
FIG. 9 is a waveform chart showing an output signal of the vibration applying circuit 144B in the agitating section of the automatic analyzing apparatus according to one embodiment of the present invention.

FIG. 8 is a waveform chart showing an output signal of the vibration signal operating means 144A in the agitating section of the automatic analyzing apparatus according to one embodiment of the present invention, and FIG. 9 is a waveform chart showing an output signal of the vibration applying circuit 144B in the agitating section of the automatic analyzing apparatus according to one embodiment of the present invention.

In FIGS. 8 and 9, the horizontal axis represents a time t and the vertical axis represents a voltage V. As shown in FIG. 8, the vibration signal operating means 144A outputs a vibration operative signal S1A in the form of a saw tooth wave to the vibration applying circuit 144B. The voltage of the saw tooth wave varies from −Δv to +Δv about a center voltage V1.

By applying such a saw tooth wave, as shown in FIG. 9, a vibration signal S2A outputted from the vibration applying circuit 144B has the oscillation frequency that becomes higher as the voltage of the vibration operative signal rises. In the case of employing a saw tooth wave, the voltage is changed at such a rate as applying vibration for the same time at any frequency in the direction in which the frequency rises, and as taking no time in the direction in which the frequency lowers. In other words, a time during which oscillation is applied is the same at any frequency within a region in which the oscillation frequency of the vibration signal varies.

Also, by providing an offset V1 to the vibration operative signal as shown in FIG. 8, the oscillation frequency of the vibration signal shown in FIG. 9 can be outputted within a frequency range of ±Δf about the center at the frequency fp3 corresponding to the offset voltage V1.

Thus, a region Y (fp3±Δf) in which the oscillation frequency varies is given by a frequency range of ±Δf with the resonance frequency fp3 of the piezoelectric transducer being at the center. In an illustrated example, the central frequency of the oscillation frequency varying region (fp3±Δf) is assumed to be in match with the resonance frequency fp3 of the piezoelectric transducer. As described above with reference to FIG. 3, however, the resonance frequency of the piezoelectric transducer differs slightly between individual piezoelectric transducers. Even with such a shift of the resonance frequency of the piezoelectric transducer to the higher or lower side, since the oscillation frequency is varied in this embodiment, the piezoelectric transducer can be vibrated at the resonance frequency to generate an ultrasonic wave without needing, e.g., a special adjustment of the oscillation frequency so long as the resonance frequency of the piezoelectric transducer is within the oscillation frequency varying region Y. Based on experimental results, no appreciable differences in effect of the operation are found between when the vibration operative signal is a saw tooth wave and that when it is a triangular wave. This means that either one of the methods having the simplest circuit configuration can be employed. Additionally, the same effect of the operation is obtained in the case of using a reversed saw tooth wave.

The third operation of frequency modulation performed by the vibration signal operating means in the agitating section of the automatic analyzing apparatus of this embodiment will be described below with reference to FIGS. 10 and 11.

Figure 10:
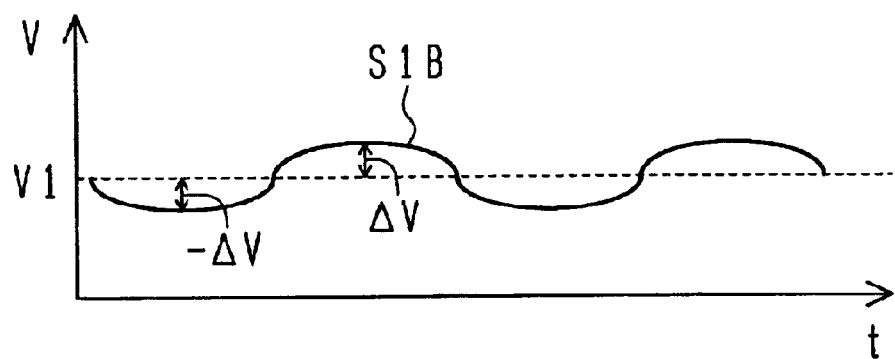
FIG. 10 is a waveform chart showing an output signal of the vibration signal operating means 144A in the agitating section of the automatic analyzing apparatus according to one embodiment of the present invention.
Figure 11:
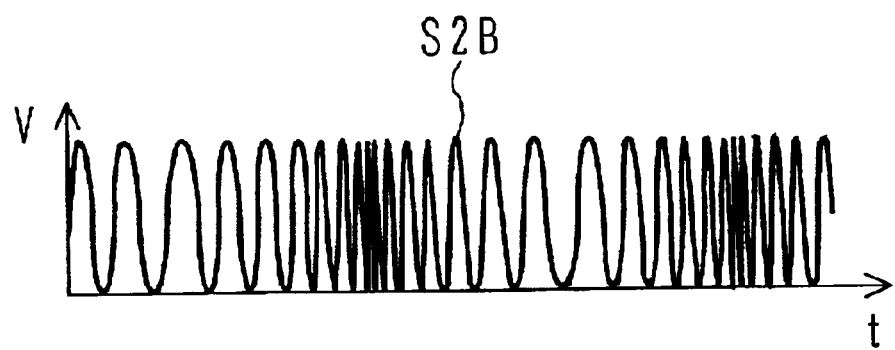
FIG. 11 is a waveform chart showing an output signal of the vibration applying circuit 144B in the agitating section of the automatic analyzing apparatus according to one embodiment of the present invention.

FIG. 10 is a waveform chart showing an output signal of the vibration signal operating means 144A in the agitating section of the automatic analyzing apparatus according to one embodiment of the present invention, and FIG. 11 is a waveform chart showing an output signal of the vibration applying circuit 144B in the agitating section of the automatic analyzing apparatus according to one embodiment of the present invention.

In FIGS. 10 and 11, the horizontal axis represents a time t and the vertical axis represents a voltage V. As shown in FIG. 10, the vibration signal operating means 144A outputs a vibration operative signal SIB in the form of a sine wave to the vibration applying circuit 144B. The voltage of the sine wave varies from −Δv to +Δv about a center voltage V1.

By applying such a sine wave, as shown in FIG. 11, a vibration signal S2B outputted from the vibration applying circuit 144B has the oscillation frequency that changes at a rate in accordance with a cosine wave. Therefore, a time during which oscillation is applied is longer at some frequency. If the vibration operative signal SIB is exactly a sine wave with the phase of 0 radian, a time during which oscillation is applied is longer at the lowest and highest frequency in the preset oscillation frequency varying region, and is shorter near the central frequency therein. Such a variation is not efficient from the theoretical point of view. Based on experimental results, however, no appreciable differences in effect of the operation are found in comparison with the case of using a triangular wave as the vibration operative signal. This means that either one of the methods having the simplest circuit configuration can be employed.

The operation of drive voltage control executed by the drive circuit in the agitating section of the automatic analyzing apparatus of this embodiment will be described below with reference to FIG. 12.

Figure 12:
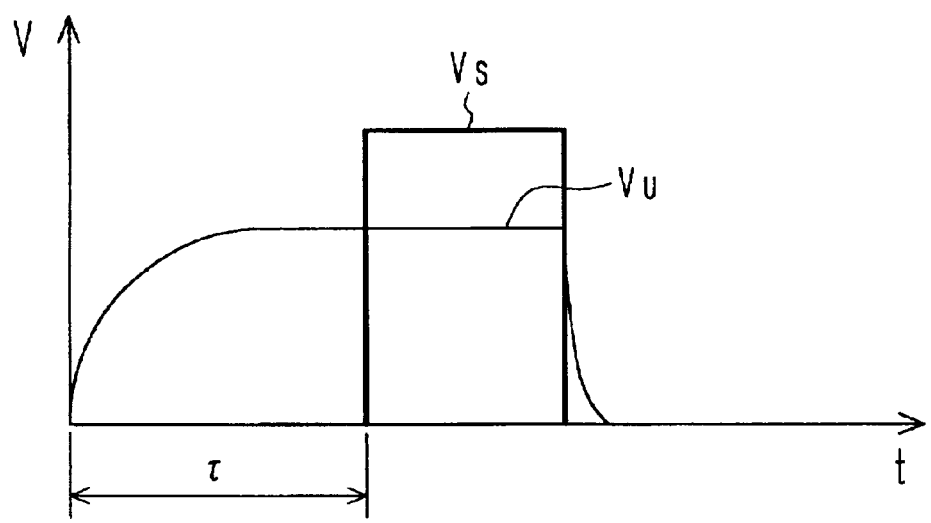
FIG. 12 is a waveform chart showing the operation of drive voltage control executed by a drive circuit in the agitating section of the automatic analyzing apparatus according to one embodiment of the present invention.

FIG. 12 is a waveform chart showing the operation of drive voltage control executed by the drive circuit in the agitating section of the automatic analyzing apparatus according to one embodiment of the present invention.

An acoustic flow can also be generated in a liquid under analysis by employing only one of the piezoelectric transducers 141, 142 shown in FIG. 1. As a method for realizing more effective agitation in a shorter time, this embodiment employs an agitating method for producing swirl flows based on multi-directional irradiation in which the ultrasonic wave 141a is irradiated from below the reaction container, and the ultrasonic wave 142a is irradiated laterally toward the liquid in an area where the liquid surface within the reaction container rises with the ultrasonic wave 141a.

Further in this embodiment, the drive voltage outputted from the drive circuit 144C is controlled to adjust the timings of the irradiation from below and the lateral irradiation so that more effective agitation is achieved. More specifically, in this embodiment, more satisfactory agitation is realized by slowly raising a voltage Vu applied for the irradiation from below, and then applying a voltage Vs for the lateral irradiation after a delay time τ of about 0.5 sec, although the delay time depends on the shape of the reaction container 132 and the viscosity of a liquid under analysis. The cutoff timings of the voltage Vu applied for the irradiation from below and the voltage Vs applied for the lateral irradiation are controlled by the control unit 110 so that the cutoff timings can be optionally set during a period of time in which the next reaction container comes to a position where it is subjected to agitation.

The construction of an automatic analyzing apparatus according to another embodiment of the present invention will be described below with reference to FIGS. 13 and 14.

The overall construction of the automatic analyzing apparatus of this embodiment is the same as that shown in FIG. 1. The following description is therefore made of the construction and operation of an agitating section of the automatic analyzing of this embodiment with reference to FIGS. 13 and 14.

Figure 13:
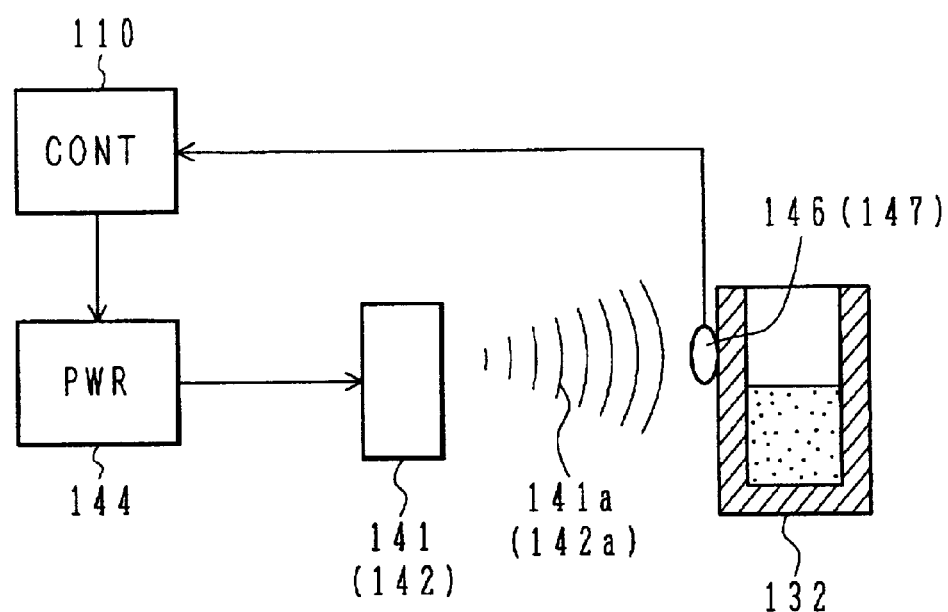
FIG. 13 is a block diagram showing the construction of an agitating section of an automatic analyzing apparatus according to another embodiment of the present invention.
Figure 14:
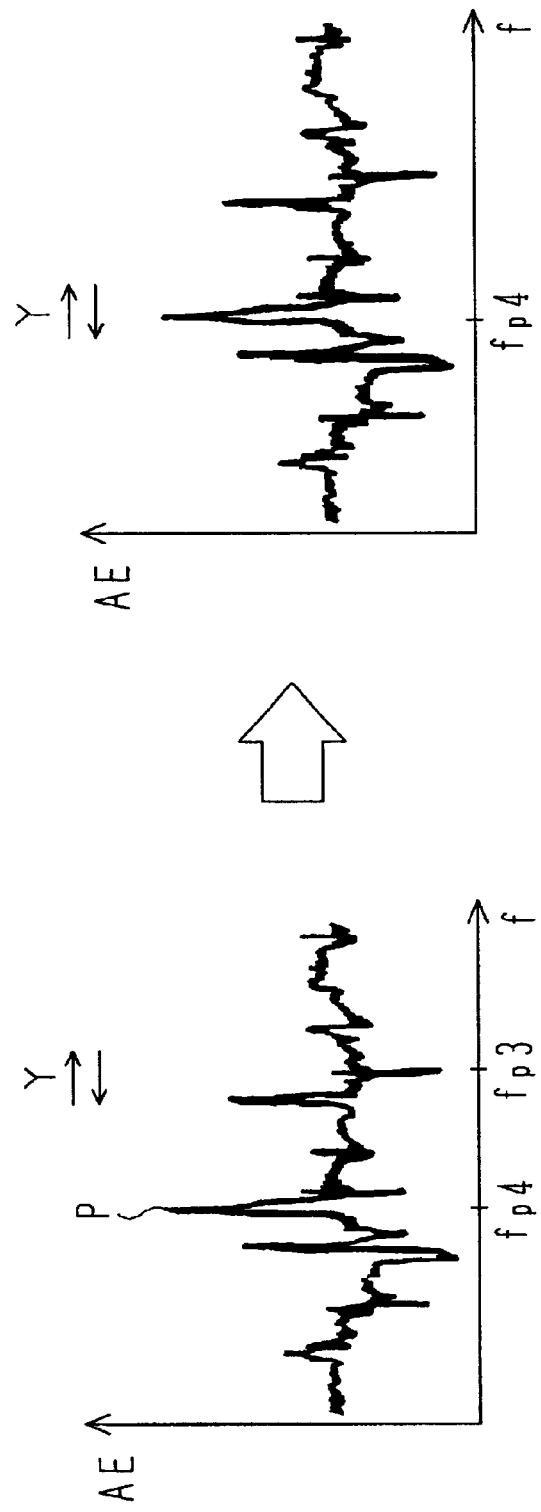
FIG. 14 is a chart for explaining the operation of an agitating section of an automatic analyzing apparatus according to another embodiment of the present invention.

FIG. 13 is a block diagram showing the construction of the agitating section of the automatic analyzing apparatus according to another embodiment of the present invention, and FIG. 14 is a chart for explaining the operation of the agitating section of the automatic analyzing apparatus according to another embodiment of the present invention. The same characters as those in FIG. 2 denote the same components.

First, the construction of the agitating section of the automatic analyzing apparatus of this embodiment will be described below with reference to FIG. 13.

This embodiment is intended to detect and compensate for changes of the frequency characteristic over time, which is caused upon changes of the resonance frequency due to flaws, depolarization, deteriorations, etc. occurred in the piezoelectric transducer, serving as the ultrasonic wave generator, after installation thereof.

In this embodiment, as shown in FIG. 13, a sensor 146 capable of measuring the intensity of an ultrasonic wave, such as a hydrophone, is provided in the agitating section in addition to the piezoelectric transducer 141, the power supply unit 144, and the control unit 110 shown in FIG. 2. The sensor 146 is installed in an area of the reaction container 132, to which the ultrasonic wave 141a is irradiated. Although only the piezoelectric transducer 141 is shown in FIG. 13, the two piezoelectric transducers 141, 142 are actually provided as with FIG. 2. The piezoelectric transducer 141 is disposed below the reaction container 132 to irradiate the ultrasonic wave 141a from below so that the liquid surface of the mixture of the sample Sa and the reagent Re rises. Also, the piezoelectric transducer 142 is disposed laterally of the reaction container 132 to irradiate the ultrasonic wave 142a toward the liquid in an area where the liquid surface rises with the ultrasonic wave from the piezoelectric transducer 141. The swirl flows F are thereby produced due to the acoustic radiant pressures for agitation of the mixture. The following description will be made in connection with the piezoelectric transducer 141 as an example.

The sensor 146 detects the intensity of the ultrasonic wave 141a generated when the piezoelectric transducer 141 is driven with a voltage applied from the power supply circuit 144 at frequencies within the preset oscillation frequency varying region. The control unit 110 determines whether the intensity of the ultrasonic wave detected by the sensor 146 falls within a preset intensity range. When the detected intensity is greater or smaller than the preset intensity range, the control unit 110 performs control so that the detected intensity falls within the objective intensity range. Herein, since the oscillation frequency applied to the piezoelectric transducer is subjected to frequency modulation, the intensity of the irradiated ultrasonic wave changes over time. In view of that fact, the sensor 146 detects a maximum value of the intensity of the irradiated ultrasonic wave. Alternatively, the sensor 146 may detect an average value of the intensity of the irradiated ultrasonic wave. While a hydrophone or the like measures the intensity of the ultrasonic wave directly, the sensor 146 may be constituted as a sensor for measuring the intensity of the ultrasonic wave indirectly. Such a sensor may be a temperature sensor, e.g., a thermocouple, for measuring the temperature of the reaction container heated by the ultrasonic wave.

The method of controlling the intensity of the ultrasonic wave by the control unit 110 is divided into two, i.e., one of varying frequency and the other of varying voltage.

First, the method of varying the frequency of the applied voltage will be described with reference to FIG. 14. For example, the intensity of the ultrasonic wave shown in FIG. 4 represents the result measured before changes over time occur. At that time, the resonance frequency is fp3. On the other hand, the left side of FIG. 14 represents the intensity of the ultrasonic wave measured after the resonance frequency has changed to fp4 due to changes over time. It is here assumed that the resonance frequency shifts to, for example, the lower frequency side due to changes over time. In such a case, if the frequency modulation is performed within the frequency varying region Y with the central frequency remaining at fp3, the intensity of the ultrasonic wave will be deficient. When a deficiency occurs in the intensity of the ultrasonic wave, the control unit 110 controls the vibration signal operating means 144A in the power supply circuit 144 such that the central frequency of the frequency varying region is gradually shifted from fp3 to fp4, for example, while the width of the frequency varying region remains Y. With that control, the intensity of the ultrasonic wave can be increased over the predetermined intensity range. Also, when the intensity of the ultrasonic wave is too large, the intensity can be reduced by varying the central frequency of the frequency varying region in a reversed manner to the above case, or by narrowing the frequency varying region.

Further, as shown in FIG. 3, when the intensity of the ultrasonic wave is represented by a simple graph free from noise components, the frequency modulation change can be changed so as to contain the resonance frequency fp4, to which a shift has occurred, within the original frequency varying region Y, by first widening the frequency varying region so as to contain the shifted resonance frequency, and then gradually changing the central frequency. Thus, in this embodiment, when the intensity of the ultrasonic wave is deficient or excessive, an ultrasonic-wave intensity signal is fed back to eliminate the deficient or excessive intensity of the ultrasonic wave by changing the frequency varying region and/or the central frequency thereof.

Next, the method of varying the amplitude of the applied voltage will be described with reference to FIG. 4. The left side of FIG. 14 represents the frequency varying region Y when the intensity of the ultrasonic wave is deficient. At that time, the central frequency of the frequency varying region Y is assumed to be, for example, fp3. When a deficiency occurs in the intensity of the ultrasonic wave, the control unit 110 controls the drive circuit 144C in the power supply unit 144 such that the amplitude of the voltage applied from the drive circuit 144C to the piezoeletric transducer 141 is gradually increased while keeping the width and central frequency of the frequency varying region remain at Y and fp3, respectively. With that control, the intensity of the irradiated ultrasonic wave can be increased so as to fall within the predetermined intensity range. Also, when the intensity of the ultrasonic wave is too large, the intensity can be reduced by reducing the applied voltage. Thus, in this embodiment, when the intensity of the ultrasonic wave is deficient or excessive, an ultrasonic-wave intensity signal is fed back to eliminate the deficient or excessive intensity of the ultrasonic wave by varying the voltage applied to the piezoelectric transducer.

Further, the method of varying the central frequency of the frequency modulation, the method of varying the frequency varying region, and the method of varying the amplitude of the applied voltage may be used in a combined manner.

If the detected result does not fall within the objective intensity range of the ultrasonic wave within a preset time by any of the method of varying the central frequency of the frequency modulation, the method of varying the frequency varying region, and the method of varying the amplitude of the applied voltage, this is regarded as indicating the occurrence of any abnormality in the power supply unit 144 or the piezoelectric transducers 141, 142. Then, an alarm is issued using, e.g., the monitor 112 and the speaker 114 shown in FIG. 1.

With this embodiment, as described hereinabove, even when there are variations or disorders in frequency characteristics of the intensities of the ultrasonic waves generated from individual ultrasonic wave generators used in the agitating section of the automatic analyzing apparatus, the intensity of the generated ultrasonic wave is averaged by varying the frequency of the voltage applied to the ultrasonic wave generator over an any desired frequency range. Therefore, the satisfactory agitation state and analyzed results can be obtained regardless of differences in frequency characteristics of the individual ultrasonic wave generators.

Also, a sensor for measuring the intensity of the ultrasonic wave generated from the ultrasonic wave generator is provided, and a measured ultrasonic-wave intensity signal is fed back to change the central frequency and oscillation frequency range of the modulated voltage applied to ultrasonic wave generator, or to change the amplitude of the applied voltage. As a result, the satisfactory agitation state and analyzed results can be obtained regardless of changes in characteristics of the ultrasonic wave generator used.

Further, a sensor for measuring the intensity of the ultrasonic wave generated from the ultrasonic wave generator is provided, and a measured ultrasonic-wave intensity signal is employed to detect the occurrence of any abnormality in the ultrasonic wave generator or the power supply unit.

Reliability of the automatic analyzing apparatus can be hence improved.

INDUSTRIAL APPLICABILITY

According to the present invention, adjustment work needed in an agitating section can be simplified, and satisfactory analyzed results can be obtained regardless of differences in frequency characteristics of ultrasonic wave generators used for ultrasonic agitation.

Also, according to the present invention, the necessity of readjustment to compensate for, e.g., changes in characteristics of the ultrasonic wave generator over time is eliminated, and maintainability can be improved.

What is claimed is:

1. An automatic analyzing apparatus comprising an agitating section for agitating liquid in a reaction vessel with an ultrasonic wave generated from an ultrasonic wave generator connected to a power supply unit, and an analyzing section for measuring a reaction product produced as an analysis target from the reagent and the sample under agitation, and analyzing components of the sample, wherein said agitating section includes said power supply unit for applying, to said ultrasonic wave generator, a voltage having been subjected to frequency modulation at frequencies over frequency range.

2. An automatic analyzing apparatus according to claim 1, wherein said ultrasonic wave generator in said agitating section comprises a first ultrasonic wave generator disposed below a reaction container, and a second ultrasonic wave generator disposed laterally of said reaction container, and said power supply unit applies, to at least said second ultrasonic wave generator, a voltage having been subjected to frequency modulation.

3. An automatic analyzing apparatus according to claim 1, further comprising a sensor for measuring the intensity of the ultrasonic wave irradiated to the liquid in the reaction vessel from said ultrasonic wave generator, and a control unit coupled to the sensor for controlling said power supply unit so that the intensity of the ultrasonic wave detected by said sensor is held at a predetermined intensity.

4. An automatic analyzing apparatus according to claim 3, wherein said control unit controls a frequency range and a central frequency of a voltage applied from said power supply unit to said ultrasonic wave generator.

5. An automatic analyzing apparatus according to claim 3, wherein said control unit controls an amplitude of a voltage applied from said power supply unit to said ultrasonic wave generator.

6. An automatic analyzing apparatus according to claim 3, wherein said control unit issues an alarm indicating the occurrence of any abnormality in said agitating section if the detected intensity of the ultrasonic wave departs from a predetermined intensity in spite of control of said power supply unit.

7. An automatic analyzing apparatus according to claim 1, wherein said power supply unit applies said voltage in a triangular wave form.

8. An automatic analyzing apparatus according to claim 1, wherein said power supply unit applies said voltage in a saw tooth wave form.

9. A automatic analyzing apparatus according to claim 1, wherein said power supply unit applies said voltage in a sine wave form.

* * * * *